United States Patent [19]

Kalchauer et al.

[11] Patent Number: 5,210,255
[45] Date of Patent: May 11, 1993

[54] PROCESS FOR THE PREPARATION OF METHYLCHLOROSILANES

[75] Inventors: Wilfried Kalchauer; Bernd Pachaly, both of Burghausen, Fed. Rep. of Germany

[73] Assignee: Wacker-Chemie GmbH, Munich, Fed. Rep. of Germany

[21] Appl. No.: 944,575

[22] Filed: Sep. 14, 1992

[30] Foreign Application Priority Data

Oct. 17, 1991 [DE] Fed. Rep. of Germany ....... 4134422

[51] Int. Cl.$^5$ ................................................ C07F 7/08
[52] U.S. Cl. .................................................... 556/468
[58] Field of Search ........................................ 556/468

[56] References Cited

U.S. PATENT DOCUMENTS

| | | | |
|---|---|---|---|
| 2,636,895 | 4/1953 | Walton | 556/468 |
| 2,709,176 | 5/1955 | Bluestein | 556/468 |
| 3,639,105 | 2/1972 | Atwell et al. | 556/468 X |
| 3,772,347 | 12/1971 | Atwell et al. | 556/468 |
| 4,059,608 | 11/1977 | Calas et al. | 556/468 |
| 4,958,040 | 9/1990 | Yoshioha et al. | 556/468 X |

Primary Examiner—Paul F. Shaver

[57] ABSTRACT

A process for the preparation of methylchlorosilanes which comprises reacting methylchlorodisilanes with hydrogen chloride in the presence of a metal from subgroup VIII of the Periodic Table as a catalyst. Preferably, finely divided palladium present on a support such as charcoal or activated carbon is used as a catalyst.

5 Claims, No Drawings

PROCESS FOR THE PREPARATION OF METHYLCHLOROSILANES

The invention relates to a process for the preparation of methylchlorosilanes and more particularly to a process for preparing methylchlorosilanes by cleavage of methylchlorodisilanes.

BACKGROUND OF THE INVENTION

Methylchlorosilanes are obtained in the process described by Rochow by reacting methyl chloride with elemental silicon. This reaction produces disilanes as a by-product.

In U.S. Pat. No. -A3,772,347 (issued Nov. 13, 1973, to W. H. Atwell et al., Dow Corning Corporation), a process for the cleavage of disilanes is described which comprises cleavage of the Si-Si bond in the disilane with the formation of a silicon-carbon bond and a silicon-chlorine bond in accordance with the following reaction scheme:

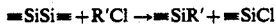

In these formulas, R' is an alkyl radical or hydrogen. The catalysts used are transition-metal complexes, such as phosphinepalladium complexes or finely divided platinum or palladium, which may be present on a support such as carbon.

According to Example 3 of U.S. Pat. No.-A 3,772,347, a methylchloro-silane mixture is reacted with hydrogen chloride in the presence of a phosphinepalladium complex. About 25% by weight of the methylchlorosilanes obtained contain Si-bonded hydrogen.

Therefore, it is an object of the present invention to provide a process for the cleavage of methylchlorodisilanes in which methylchlorosilanes which are free of Si-bonded hydrogen are obtained.

SUMMARY OF THE INVENTION

The foregoing object and others which are apparent from the following description are accomplished in accordance with this invention, generally speaking, by providing a process for preparing methylchlorosilanes by reacting methylchlorodisilanes with hydrogen chloride in the presence of a metal from subgroup VIII of the Periodic Table as a catalyst.

DESCRIPTION OF THE INVENTION

The advantages of the process of this invention are that the monosilanes obtained are the desired products of the direct synthesis of silanes, i.e., the disilanes formed in the Rochow process as a by-product are converted into industrially useful monosilanes. For example, combustion of the disilanes is omitted, thereby enhancing the environment; only short reaction times are necessary for the process; the desired monosilanes are obtained in high yields and the catalyst is present in solid form, i.e., the reaction is catalyzed heterogeneously, thereby providing for easy separation of the catalyst from the reaction residues and distillation reaction columns filled with catalyst can be used.

Examples of metals of subgroup VIII of the Periodic Table are platinum, palladium, rhodium and ruthenium, in which palladium is the preferred catalyst.

The metals are preferably used in finely divided form and are preferably present on supports.

Examples of supports are activated carbon, charcoal, inorganic oxides, such as silica, alumina, titanium dioxide, zirconium dioxide and silicates; carbonates, such as calcium carbonate and barium carbonate; sulfates, such as barium sulfate; and organic supports, such as polyethyleneimines filled with silica. Charcoal and activated carbon are preferred supports.

Catalysts of this type, in which the finely divided metals are present on supports, are commercially available, such as, for example, palladium on barium sulfate (5% by weight of palladium/ 95% by weight of barium sulfate) from Strem Chemicals GmbH or, for example, platinum on activated carbon (3% by weight of platinum/ 97% by weight of activated carbon) from Johnson Matthey GmbH.

The metal concentration on the supports is preferably from 0.8 to 10% by weight, based on the total weight of the catalyst; however, higher or lower concentrations can also be used.

The methylchlorodisilanes used in the process of this invention are those of the general formula $(CH_3)_nSi_2Cl_{6-n}$, in which n is an integer of from 2 to 6.

Examples of methylchlorodisilanes are those of the formulas $MeCl_2SiSiCl_2Me$, $Me_2ClSiSiCl_2Me$, $Me_2ClSiSiClMe_2$, $Me_3SiSiCl_2Me$, $Me_3SiSiClMe_2$ and $Me_3SiSiMe_3$, in which Me is a methyl radical.

The direct synthesis of a silane from methyl chloride and elemental silicon according to the Rochow process, produces methylchlorodisilanes as by-product in the high-boiling residue, from which they can be isolated and used in the process of this invention.

It is possible to use one type of methylchlorodisilane or a mixture of at least two methylchlorodisilanes. The methylchloro-disilanes or their mixtures can be used in liquid form or in gaseous form.

In the process of this invention, hydrogen chloride is preferably used in amounts of at least 2 mols, preferably from 2.5 to 10 mols, per mol of methylchlorodisilane used.

In the process of this invention, methylchlorosilanes of the general formula $(CH_3)_mSiCl_{4-m}$, in which m is 1, 2 or 3, are preferably prepared.

Examples of methylchlorosilanes are those of the formulas $MeSiCl_3$, $Me_2SiCl_2$ and $Me_3SiCl$, in which Me is a methyl radical.

The process of this invention is preferably carried out under an inert gas atmosphere, such as a nitrogen, argon or helium atmosphere, preferably under a nitrogen or argon atmosphere. The process of this invention is carried out at a temperature of preferably from 50 to 250° C., and more preferably from 100 to 200° C. and preferably at the pressure of the surrounding atmosphere. However, it is also possible to use higher or lower pressures.

In the process of this invention, insert organic solvents, such as toluene, xylene, octane, decane or petroleum ether of various boiling fractions, can be used, although it is preferred not to use them.

The catalyst used according to this invention can be used in the liquid phase or in the gas phase.

In the process carried out in the liquid phase, the catalyst is preferably added in amounts of less than 0.1 mol %, preferably in amounts of 0.01 to 0.05 mol %, based on the elemental metal and the entire molar amount of the liquid methylchlorodisilanes used.

The catalyst can be easily separated from the high-boiling residues, for example by filtration.

In the process carried out in the gas phase, a distillation reaction column filled with catalyst material, where the catalyst metal is present on a support can be used. This procedure has the advantage that the catalyst no longer has to be separated from the high-boiling reaction residues and the methylchlorosilanes thus formed in the reaction are simultaneously purified by distillation upon passing through the column.

The process of this invention can be carried out batchwise, semi-continuously or continuously.

EXAMPLE 1

About 310 g of a methylchlorodisilane mixture comprising
1,0% by weight of pentamethylchlorodisilane,
5.2% by weight of 1,1,1,2-tetramethyldichlorodisilane,
87.5% by weight of 1,1,2,2-tetramethyldichlorodisilane,
2.3% by weight of 1,1,2-trimethyltrichlorodisilane and
3.4% by weight of 1,2-dimethyltetrachlorodisilane
and 0.03 mol % of palladium, based on the entire molar amount of the disilane used, in the form of 1.06 g of palladium on activated carbon (5% by weight of palladium/95% by weight of activated carbon) were initially introduced under a nitrogen atmosphere into a three-neck flask fitted with thermometer, gas introduction tube and metallized-glass column fitted with distillation head. The mixture was heated to 140° C. with stirring, and hydrogen chloride was introduced into the mixture in an amount of about 25 liters per hour. The reaction products were distilled off from the reaction flask via the column, condensed and analyzed by gas chromatography and by $^1$H-NMR spectroscopy. After a reaction time of 4.5 hours, 271 g of distillate having the following composition were obtained:
95.6% by weight of dimethyldichlorosilane (Me$_2$SiCl$_2$),
2.3% by weight of methyltrichlorosilane (MeSiCl$_3$) and
1.3% by weight of trimethylchlorosilane (Me$_3$SiCl).

COMPARISON EXAMPLE 1

The procedure of Example 1 was repeated, except that 0.03 mol % of palladium (based on the entire molar amount of the disilane mixture) was used in the form of 0.053 g of tetrakis(triphenylphosphine)palladium instead of 0.03 mol % of palladium in the form of palladium on activated carbon. After a reaction time of 4.5 hours, about 26 g of distillate having the following composition were obtained:
6.5% by weight of methyltrichlorosilane (MeSiCl$_3$),
4.2% by weight of dimethyldichlorosilane (Me$_2$SiCl$_2$),
2.8% by weight of methyldichlorosilane (MeHSiCl$_2$) and
15.3% by weight of dimethylchlorosilane (Me$_2$HSiCl).

COMPARISON EXAMPLE 2

The procedure of Example 1 was repeated, except that 75 g of a methylchlorodisilane mixture comprising
0.8% by weight of 1,2-dimethyltetrachlorodisilane,
0.9% by weight of 1,1,2-trimethyltrichlorodisilane,
91.2% by weight of 1,1,2,2-tetramethyldichlorodisilane,
1.3% by weight of 1,1,1,2-tetramethyldichlorodisilane and
1.0% by weight of 1,1,1,2,2-pentamethylchlorodisilane
were substituted for the methylchlorodisilane mixture of Example 1 and 0.35 mol % of palladium (based on the entire molar amount of the disilane mixture used) in the form of 1.5 g of tetrakis(triphenylphosphine)palladium was substituted for the 0.03 mol % of palladium in the form of palladium on activated carbon. The mixture was heated to 143° C. with stirring, and hydrogen chloride was introduced into the mixture in amounts of 15 liters per hour. After a reaction time of 3 hours, 29 g of distillate having the following composition were obtained:
16.2% by weight of trimethylchlorosilane (Me$_3$SiCl),
50.0% by weight of dimethyldichlorosilane (Me$_2$SiCl$_2$),
1.2% by weight of methyldichlorosilane (MeHSiCl$_2$) and
30.1% by weight of dimethylchlorosilane (Me$_2$HSiCl).

EXAMPLE 2

The experimental apparatus described in Example 1 was used, except that the catalyst comprising 12 g of granular carbon coated with 1.4% by weight of palladium was placed in the column, and the disilane mixture was continuously metered into the reaction flask. The amount of disilane mixture being metered in corresponded to the amount of monosilane mixture being distilled off. Hydrogen chloride was metered in in an amount of about 78 liters per hour. A disilane mixture of the following composition was used:
35.7% by weight of MeCl$_2$SiSiCl$_2$Me,
42.6% by weight of Me$_2$ClSiSiCl$_2$Me,
6.9% by weight of Me$_2$ClSiSiClMe$_2$,
0.9% by weight of Me$_3$SiSiCl$_2$Me and
1.4% by weight of Me$_3$SiSiClMe$_2$
(the remainder mainly comprises monosilanes and siloxanes) After 13 hours, the reaction which was carried out continuously was stopped. Overall, 950 g of disilane mixture were added dropwise and 980 g of distillate of the following composition were obtained:
1% by weight of Me$_3$SiCl,
31% by weight of Me$_2$SiCl$_2$ and
67% by weight of MeSiCl$_3$. (Me represents a methyl radical.)

What is claimed is:

1. A process for preparing methylchlorosilanes which comprises reacting methylchlorodisilanes with hydrogen chloride in the presence of a catalytic amount of a metal from subgroup VIII of the Periodic Table.

2. The process of claim 1, wherein the metal is present on a support.

3. The process of claim 1, wherein the metal is palladium.

4. The process of claim 1, wherein the methylchlorosilanes obtained are those of the general formula $$(CH_3)_m SiCl_{4-m}$$

in which m is an integer from 1 to 3.

5. The process of claim 1, wherein the methylchlorodisilanes used are those of the general formula $$(CH_3)_n Si_2 Cl_{6-n}$$

in which n is an integer from 2 to 6.

* * * * *